United States Patent [19]

Owsley et al.

[11] 4,107,220
[45] Aug. 15, 1978

[54] GAS PHASE NITRATION OF CHLOROBENZENE

[75] Inventors: Dennis C. Owsley, St. Louis; Jordan J. Bloomfield, Creve Coeur, both of Mo.

[73] Assignee: Monsanto Company, St. Louis, Mo.

[21] Appl. No.: 848,547

[22] Filed: Nov. 4, 1977

[51] Int. Cl.$^2$ ............................................. C07C 79/12
[52] U.S. Cl. ................................................... 260/646
[58] Field of Search .................... 260/646; 252/455 Z; 424/349

[56] References Cited

U.S. PATENT DOCUMENTS

| | | | |
|---|---|---|---|
| 3,928,476 | 12/1975 | Shimada et al. | 260/646 |
| 3,966,830 | 6/1976 | Shimada et al. | 260/646 |

*Primary Examiner*—Benjamin R. Padgett
*Assistant Examiner*—Irwin Gluck
*Attorney, Agent, or Firm*—Scott J. Meyer; James W. William, Jr.

[57] ABSTRACT

A method is provided for controlling the para:ortho isomer distribution in nitrochlorobenzene product mixtures by the vapor phase nitration of chlorobenzene in the presence of a molecular sieve catalyst having a relatively small pore size ranging from about 5 Å to about 10 Å.

7 Claims, No Drawings

GAS PHASE NITRATION OF CHLOROBENZENE

BACKGROUND OF THE INVENTION

This invention relates to the nitration of chlorobenzene and, more particularly, to a method for controlling the para:ortho isomer distribution of nitrochlorobenzenes by the vapor phase nitration of chlorobenzene in the presence of small pore size molecular sieve catalysts.

Nitrochlorobenzenes are widely used intermediates in organic synthesis including materials for producing dyes, pharmaceuticals and synthetic fibers. The usual methods for making nitrochlorobenzenes are liquid phase reactions employing mixed acids. A sulfuric/nitric acid mixture is the chief industrial nitrating agent. Other mixed acids for nitration of monochlorobenzene are acetic/nitric acid mixtures as described, for example, in U.S. Pat. No. 3,180,900. In U.S. Pat. No. 3,928,476, the latter type nitration is conducted over silica-alumina or alumina supports.

Vapor phase nitration also has been employed heretofore. It has been used for the nitration of paraffins as described by Hass et al. *Ind. Eng. Chem.* 28 (3), 340-44 (1936), and U.S. Pat. No. 1,967,667; and for the nitration of benzene and toluene as disclosed by McKee and Wilhelm, *Ind. Eng. Chem.* 28 (6), 662-67 (1936), and U.S. Pat. No. 2,109,873. McKee and Wilhelm catalyzed their reaction with silica gel, with best results being reported by use of 14 mesh material. Bauxite and alumina were reported to be ineffective catalysts in the vapor phase nitration of benzene.

Further background information on conventional nitration methods can be had by reference to Albright and Hanson, "Industrial and Laboratory Nitrations," ACS Symposium Series 22, 1976, American Chemical Society, Washington, D.C.

Although the prior art discloses methods for increasing the proportion of para isomer in nitrochlorobenzene product mixtures from the usual 65% para: 35% ortho distribution, it does not teach convenient means for controlling the isomer distribution within a broad range.

BRIEF DESCRIPTION OF THE INVENTION

In accordance with the present invention, a method is provided for controlling the para:ortho isomer distribution in nitrochlorobenzene product mixtures by the vapor phase nitration of chlorobenzene in the presence of a molecular sieve catalyst having a relatively small pore size of from about 5 Å to about 10 Å. This method facilitates control of the isomer distribution in predetermined relative proportions within a broad range.

DETAILED DESCRIPTION OF THE INVENTION

The nitrating agents used in the method of the present invention are the gaseous oxides of nitrogen higher than NO such as $NO_2$, $N_2O_3$, and $N_2O_4$. Of these, $NO_2$ is preferred.

The molecular sieve catalysts employed in accordance with this invention are synthetic zeolites which are aluminosilicate compounds having a well-defined crystalline structure. The fundamental structural units are silicon and aluminum atoms tetrahedrally coordinated with 4 oxygen atoms. The silicate and aluminate units are typically joined to form 4- and 6-membered rings of oxygen atoms forming a simple and consistent arrangement of polyhedra. Each polyhedron is a three-dimensional array of tetrahedra in a definite geometric form. The manner in which the polyhedra are connected governs the size of the pore openings in the crystal lattice. The structure and synthesis of molecular sieve catalysts is well understood in the art; further information thereon is readily available and can be had by reference to a general text on the subject matter such as, for example, Donald W. Breck, "Zeolite Molecular Sieves," John Wiley and Sons, New York, N.Y., 1974.

In accordance with the present invention, the pore size of the molecular sieve preferably should range from about 5 Å to about 10 Å. Use of a substantially smaller pore size molecular sieve or use of macroporous silica or alumina is ineffective for producing any nitrochlorobenzene under conditions in which the molecular sieves having 5 Å to 10 Å pore size produce the desired product.

Illustrative examples of the structure and synthesis of conventional molecular sieve catalysts suitable for use in this invention can be had by reference to U.S. Pat. Nos. 2,882,243; 2,882,244; 3,130,007; and 3,216,789; all of which are incorporated herein by reference.

Various examples of suitable molecular sieve catalysts which are commercially available are:

"Zeolon 900-H" (8-9 Å pore size) from Norton Company;
"AW-500 Sieve" (5 Å pore size) from Union Carbide corp.;
"Zeolon 300" (4-8 Å pore size; sodium site has 4 Å pore size, hydrogen site has 8 Å pore size) from Norton Company; and
"13X Molecular Sieve" (10 Å pore size) from Union Carbide Corp.

It will be appreciated that the invention is not limited to the aforesaid specific molecular sieves and that other suitable molecular sieves having relatively small pore sizes can be readily selected by the person skilled in the art in the light of the aforesaid disclosure and the specific illustrative examples provided hereinafter. It will also be appreciated that the pore size of the molecular sieve can vary somewhat from the preferred 5 Å to 10 Å range specified above and will depend, in part, on the structure of the specific molecular sieve selected.

The method of the present invention can be carried out by continuously passing a vaporous mixture of the chlorobenzene and nitrating agent over a bed of the molecular sieve catalyst while maintaining a temperature of from about 190° C to about 290° C and separating the thus formed nitrochlorobenzene from said vaporous mixture.

The reactant chlorobenzene can be preheated to form a vapor which is then admixed with gaseous $NO_2$ in a suitable reactor in predetermined relative proportions. Vaporous chlorobenzene can be conveniently swept into the reactor at a constant rate by a stream of inert gas such as nitrogen, which can be dry or saturated with water vapor, and thence admixed with a continuous stream of $NO_2$ before contacting the heated catalyst bed. The reactants can be charged into the reactor at any suitable space velocity.

The relative proportions of reactants generally can range from about 1 to 3 moles of $NO_2$ per mole of chlorobenzene and, preferably, a ratio of about 2.4 to one is used.

Typical space velocities which have been found suitable for the method of the present invention range from about 1.45 × 10$^{-5}$ to about 6.58 × 10$^{-6}$ cu. ft. per second of chlorobenzene; from about 1.30 × 10$^{-4}$ to about 8.24 × 10$^{-5}$ cu. ft. per second of NO$_2$; and from about 1.18 × 10$^{-4}$ to about 7.06 × 10$^{-4}$ cu. ft. per second of nitrogen.

It should be understood that the invention is not limited to the aforesaid specific temperature range, space velocities, mol proportions of reactants, and the carrier gas and water vapor variables. These conditions can vary widely and will depend, in part, on the specific molecular sieve selected. That is, the performance of a given molecular sieve may be affected by changes in space velocity, NO$_2$ concentration, temperature, and the presence or absence of water vapor. For example, the response of the aforesaid Zeolon 900-H sieve is a complex function of all of the above conditions, whereas the ortho/para ratio of the nitrochlorobenzene product obtained by using the aforesaid AW-500 sieve is substantially less affected by changes in these conditions.

When water saturated nitrogen is used in the carrier gas, the Zeolon 300 sieve does not nitrate chlorobenzene. With this sieve, higher space velocities increase the para content at 235° C, while at 280° C the ortho content is raised by higher space velocities.

The performance of the 13X molecular sieve is affected primarily by temperature; thus, higher temperatures result in higher para content at lower conversion.

In general, dilution of the NO$_2$/chlorobenzene stream with more nitrogen to where the reactants constitute ≦ 3% of the total stream causes the reaction to cease.

The following examples are provided in order to further illustrate the present invention. These examples show the preparation of nitrochlorobenzene having isomer compositions within a broad range varying from about 85% to about 43% para and from about 9% to about 57% ortho. As can be seen from these examples, the basic vapor phase reaction employing the molecular sieve catalyst of relatively small pore size is readily adaptable to provide any desired predetermined relative proportions of isomers within this range.

The reactor used in these examples consisted of a Pyrex® glass tube, ½ inch I.D. (inside diameter), 16 inches long, packed with an 8 inch bed of molecular sieve catalyst. A stream of chlorobenzene was preheated and swept into the reactor tube in a stream of nitrogen which was saturated with water vapor in most cases and dry in the other cases. Nitrogen dioxide was mixed with the chlorobenzene/nitrogen stream shortly before contact with the heated catalyst.

The products were collected in a chilled flask at the end of the tube. Analyses were performed by GLC on a Varian Associates Model 2800 instrument using a 6 foot × ⅛ inch O.D. (outside diameter) SP-1000 on 0.5% phosphoric acid treated Chrom. G programmed from 80 to 180 at a 6°/min.

EXAMPLE USING ZEOLON 900-H (8-9 Å PORE SIZE)

Example A 11,25 g (0,1 mol) of chlorobenzene at a space velocity of 1.45 × 10$^{-5}$ ft.$^3$/sec., 10.9 g (0.237 mol) of nitrogen dioxide at a space velocity of 3.53 × 10$^{-5}$ ft.$^3$/sec. and water saturated nitrogen at a space velocity of 4.42 × 10$^{-4}$ ft.$^3$/sec. at 200° C yielded 8.45 g (0.0751 mol) of unreacted chlorobenzene, 0.74 g (0.005 mol) of dichlorobenzenes and 3.81 g (0.0242 mol) of a mixture of nitrochlorobenzenes which had the following distribution: 82% para, 9% ortho, 9% meta.

EXAMPLE USING ZEOLON 900-H (8-9 Å PORE SIZE)

Example B 11.25 g (0.1 mol) of chlorobenzene at a space velocity of 1.45 × 10$^{-5}$ ft.$^3$/sec., 4.18 g (0.091 mol) of nitrogen dioxide at a space velocity of 1.30 × 10$^{-4}$ ft.$^3$/sec. and water saturated nitrogen at a space velocity of 4.42 × 10$^{-4}$ ft.$^3$/sec. yielded at 200° C 10.4 g (0.0926 mol) of unreacted chlorobenzene and 1.17 g (0.0074 mol) of nitrochlorobenzene isomers. The isomer distribution was 67.6% para and 32.4% ortho.

EXAMPLE USING ZEOLON 900-H (8-9 Å PORE SIZE)

Example C 11.25 g (0.1 mol) of chlorobenzene at a space velocity of 6.58 × 10$^{-6}$ ft.$^3$/sec., 23.9 g (0.52 mol) of nitrogen dioxide at a space velocity of 3.53 × 10$^{31\ 5}$ ft.$^3$/sec. and water saturated nitrogen at a space velocity of 4.42 × 10$^{-4}$ ft.$^3$/sec. at 200° C yielded 9.34 g (0.083 mol) of unreacted chlorobenzene and 2.68 g of nitrochlorobenzene isomers. The isomer mixture was 48% para and 52% ortho.

EXAMPLE USING ZEOLON 900-H (8-9 Å PORE SIZE)

Example D 11.25 g (0.1 mol) of chlorobenzene at a space velocity of 4.08 × 10$^{-5}$ ft.$^3$/sec., 9.4 g (0.203 mol) of nitrogen dioxide at a space velocity of 8.24 × 10$^{-5}$ ft.$^3$/sec. and water saturated nitrogen at a space velocity of 3.59 × 10$^{-4}$ ft.$^3$/sec. at 200° C yielded 9.84 g (0.0874 mol) of unreacted chlorobenzene and 1.98 g (0.0126 mol) of nitrochlorobenzene isomers. The nitrochlorobenzenes consisted of 43% para isomer and 57% ortho isomer.

EXAMPLE USING ZEOLON 900-H (8-9 Å PORE SIZE)

Example E 11.25 g (0.1 mol) of chlorobenzene at a space velocity of 1.45 × 10$^{-5}$ ft.$^3$/sec., 10.9 g (0.237 mol) of nitrogen dioxide at a space velocity of 3.53 × 10$^{-5}$ ft.$^3$/sec. and water saturated nitrogen at a space velocity of 5.30 × 10$^{-4}$ ft.$^3$/sec. at 200° C yieled 9.01 g (0.08 mol) of unreacted chlorobenzene and 3.13 g (0.02 mol) of nitrochlorobenzene isomers. The mixture consisted of 84% para, 10% ortho and 6% meta.

EXAMPLE USING AW-500 SIEVE (PORE SIZE 5 Å)

Example F 11.25 g (0.1 mol) of chlorobenzene at a space velocity of 1.45 × 10$^{-5}$ ft.$^3$/sec., 10.9 g (0.237 mol) of nitrogen dioxide at a space velocity of 3.53 × 10$^{-5}$ ft.$^3$/sec. and water saturated nitrogen at a space velocity of 7.06 × 10$^{-4}$ ft.$^3$/sec. at 290° C yielded 9.07 g (0.081 mol) of unreacted chlorobenzene and 3.06 g (0.019 mol) of nitrochlorobenzenes. The isomer mix was 51% para and 49% ortho.

EXAMPLE USING AW-500 SIEVE (PORE SIZE 5 Å)

Example G 11.25 g (0.1 mol) of chlorobenzene at a space velocity of 1.45 × 10$^{-5}$ ft.$^3$/sec., 10.9 g (0.237 mol) of nitrogen dioxide at a space velocity of 3.53 × 10$^{-5}$ ft.$^3$/sec. and water saturated nitrogen at a space velocity of 5.89 × 10$^{-4}$ ft.$^3$/sec. at 290° C yielded 9.57 g (0.085 mol) of unreacted chlorobenzene and 2.35 g (0.015 mol) of nitrochlorobenzenes. The nitrochlorobenzene consisted of 57% para and 43% ortho isomers.

EXAMPLE USING AW-500 SIEVE (PORE SIZE 5 Å)

Example H

The amounts of chlorobenzene and nitrogen dioxide as in example G at the same space velocities and water saturated nitrogen at a space velocity of 5.89 × 10$^{-4}$ ft.$^3$/sec. at 240° C yielded 8.11 g (0.072 mol) of unreacted chlorobenzene and 4.39 g (0.028 mol) of nitrochlorobenzene isomers (61% para and 39% ortho).

EXAMPLE USING AW-500 SIEVE (PORE SIZE 5 Å)

Example I

Chlorobenzene and nitrogen dioxide in the same amounts and space velocities as Example G and dry nitrogen at a space velocity of 5.89 × 10$^{-4}$ ft.$^3$/sec. at 290° C yielded 9.05 (0.08 mol) of unreacted chlorobenzene and 3.09 g (0.0196 mol) of nitrochlorobenzene isomers (58% para and 42% ortho).

EXAMPLE USING AW-500 SIEVE (PORE SIZE 5 Å)

EXAMPLE J

Chlorobenzene and nitrogen dioxide in the same amounts and space velocities as Example G and dry nitrogen at a space velocity of 7.06 × 10$^{-4}$ ft.$^3$/sec. at 290° C yielded 9.86 g (0.0876 mol) of unreacted chlorobenzene and 1.95 g (0.0124 mol) of nitrochlorobenzene isomers (56% para and 44% ortho).

EXAMPLE USING AW-500 SIEVE (PORE SIZE 5 Å)

Example K chlorobenzene, nitrogen dioxide and dry nitrogen at the same amounts and space velocities as in Example I at 240° C yielded 9.53 g (0.0847 mol) of unreacted chlorobenzene and 2.41 g (0.0153 mol) of nitrochlorobenzene isomers (60% para and 40% ortho).

EXAMPLE USING ZEOLON 300 (PORE SIZE 4–8 Å)

Example L

Chlorobenzene and nitrogen dioxide in the same amounts and at the same space velocities as in Example G and dry nitrogen at a space velocity of 2.35 × 10$^{-4}$ ft.$^3$/sec. at 235° C yielded 9.11 g (0.081 mol) of unreacted chlorobenzene, 1.42 g (0.0126 mol) of nitrochlorobenzenes (62% para, 29% ortho and 9% meta) and 0.09 g (0.006 mol) of dichlorobenzenes.

EXAMPLE USING ZEOLON 300 (PORE SIZE 4–8 Å)

Example M

Chlorobenzene and nitrogen dioxide in the same amounts and space velocities as in Example G and dry nitrogen at a space velocity of 3.53 × 10$^{-4}$ ft.$^3$/sec. at 235° C yielded 7.65 g (0.068 mol) of unreacted chlorobenzene, 0.28 g (0.0019 mol) of dichlorobenzenes and 4.88 g (0.031 mol) of nitrochlorobenzenes (77% para and 23% ortho).

EXAMPLE USING ZEOLON 300 (PORE SIZE 4–8 Å)

Example N

Chlorobenzene, nitrogen dioxide and dry nitrogen in the same amounts and space velocities as in Example L at 280° C yielded 8.81 (0.078 mol) of unreacted chlorobenzene and 3.42 g (0.022 mol) of nitrochlorobenzene isomers (79% para and 21% ortho).

EXAMPLE USING ZEOLON 300 (PORE SIZE 4–8 Å)

EXAMPLE O

Chlorobenzene, nitrogen dioxide and dry nitrogen at the same amounts and space velocities as Example M at 280° C yielded 8.63 g (0.0767 mol) of unreacted chlorobenzene, 0.28 g (0.0019 mol) of dichlorobenzenes and 3.37 g (0.0213 mol) of nitrochlorobenzenes (58% para, 25% ortho and 17% meta).

EXAMPLE USING ZEOLON 300 (PORE SIZE 4–8 Å)

Example P

Chlorobenzene and nitrogen dioxide at the same amounts and space velocities as Example M and dry nitrogen at a space velocity of 4.71 × 10$^{-4}$ ft. /sec. at 280° C yielded 7.98 g (0.0709 mol) of unreacted chlorobenzene, 0.22 g (0.0015 mol) of dichlorobenzenes and 4.36 g (0.0277 mol) of nitrochlorobenzene isomers (56% para, 29% ortho and 15% meta).

EXAMPLE USING 13X MOLECULAR SIEVE (10 Å PORE SIZE)

Example Q

Chlorobenzene and nitrogen dioxide at the same amounts and space velocities as Example G and water saturated nitrogen at a space velocity of 1.18 × 10$^{-4}$ ft.$^3$/sec. at 192° C yielded 7.45 g (0.0662 mol) of unreacted chlorobenzene, 0.31 g (0.0021 mol) of dichlorobenzenes and 4.99 g. (0.0317 mol) of nitrochlorobenzene isomers (47% para, 16% ortho and 37% meta).

EXAMPLE USING 13X MOLECULAR SIEVE (10 Å PORE SIZE)

Example R

Chlorobenzene and nitrogen dioxide at the same amounts and space velocities as Example G and water saturated nitrogen at a space velocity of 2.35 × 10$^{-4}$ ft.$^3$/sec. at 192° C yielded 8.15 g (0.0724 mol) of unreacted chlorobenzene, 0.15 g (0.001 mol) of dichlorobenzenes and 4.19 g (0.0266 mol) of nitrochlorobenzene isomers (54% para, 19% ortho and 27% meta).

EXAMPLE USING 13X MOLECULAR SIEVE (10 Å PORE SIZE)

Example S

Chlorobenzene and nitrogen dioxide at the same amounts and space velocities as Example G and water saturated nitrogen at a space velocity of 2.65 × 10$^{-4}$ ft.$^3$/sec. at 240° C yielded 10.27 g (0.0913 mol) of unreacted chlorobenzene, 0.38 g (0.0026 mol) of dichlorobenzenes, and 0.96 g (0.0061 mol) of nitrochlorobenzene isomers (62% para and 38% ortho).

EXAMPLE USING 13X MOLECULAR SIEVE (10 Å PORE SIZE)

Example T

Chlorobenzene and nitrogen dioxide at the same amounts and space velocities as Example G and water saturated nitrogen at a space velocity of $3.24 \times 10^{-4}$ ft.$^3$/sec. at 240° C yielded 10.32 g (0.0917 mol) of unreacted chlorobenzene, 0.37 g (0.0025 mol) of dichlorobenzenes and 0.90 g (0.0057 mol) of nitrochlorobenzene isomers (70% para and 30% ortho).

EXAMPLE USING 13X MOLECULAR SIEVE (10 Å PORE SIZE)

Example U

Chlorobenzene, nitrogen dioxide and dry nitrogen at the same space velocities as Example S at 240° yielded 10.32 g (0.0917 mol) of unreacted chlorobenzene, 0.02 g (0.0001 mol) of dichlorobenzenes and 1.28 g (0.0081 mol) of nitrochlorobenzene isomers (60% para and 40% ortho).

EXAMPLE USING 13X MOLECULAR SIEVE (10 Å PORE SIZE)

Example V

Chlorobenzene nitrogen dioxide and dry nitrogen in the same amounts and at the same space velocities as Example T at 240° yielded 10.09 g (0.0897 mol) of unreacted chlorobenzene and 1.62 g (0.0103 mol) of nitrochlorobenzene isomers (62% para and 38% ortho).

Example W

By way of comparison with the molecular sieves used in the above examples, various other molecular sieves having pore sizes of about 5 Å or smaller (Linde 3A, Linde 5A and Zeolon 900 sodium form) or larger than about 10 Å (macroporous silica and aluminas) yielded no nitrochlorobenzene isomers at temperatures of 190°, 240°, and 290° C and space velocities of $1.45 \times 10^{-5}$ ft.$^3$/sec. for chlorobenzene, $3.53 \times 10^{-5}$ ft.$^3$/sec. for nitrogen dioxide and $1.18 \times 10^{-4}$ to $7.06 \times 10^{-4}$ ft.$^3$/sec. for nitrogen.

Various other examples will be apparent to the person skilled in the art after reading the present disclosure without departing from the spirit and scope of the invention. All such further examples are included within the scope of the appended claims.

What is claimed is:

1. A method for the production of a nitrochlorobenzene mixture in which the para:ortho isomer distribution can be readily controlled to predetermined relative proportions within a broad range comprising the vapor phase nitration of chlorobenzene with a nitrating agent in the presence of a molecular sieve catalyst having a relatively small pore size ranging from about 5 Å to about 10 Å.

2. The method of claim 1 in which the nitrating agent is $NO_2$.

3. The method of claim 1 in which the vapor phase reaction is carried out at a temperature ranging from about 190° to about 290° C.

4. The method of claim 1 in which from about one to about three moles of nitrating agent are used per mole of chlorobenzene.

5. The method of claim 1 in which the chlorobenzene is admixed with nitrogen carrier gas prior to reaction with the nitrating agent.

6. The method of claim 5 in which the nitrogen is saturated with water vapor.

7. The method of claim 1 in which the nitrating agent is $NO_2$, the temperature ranges from about 190° to about 290° C and from about one to about three moles of $NO_2$ are used per mole of chlorobenzene.

* * * * *

UNITED STATES PATENT AND TRADEMARK OFFICE
CERTIFICATE OF CORRECTION

PATENT NO. : 4,107,220                                        Page 1 of 2

DATED : August 15, 1978

INVENTOR(S) : Dennis C. Owsley, et al

It is certified that error appears in the above-identified patent and that said Letters Patent are hereby corrected as shown below:

Columns 5 thru 8 should be deleted to insert the attached Columns 5 thru 8, respectively.

Signed and Sealed this

First Day of May 1979

[SEAL]

Attest:

RUTH C. MASON
*Attesting Officer*

DONALD W. BANNER
*Commissioner of Patents and Trademarks*

11.25 g (0.1 mol) of chlorobenzene at a space velocity of 1.45 × 10$^{-5}$ ft.$^3$/sec., 10.9 g (0.237 mol) of nitrogen dioxide at a space velocity of 3.53 × 10$^{-5}$ ft.$^3$/sec. and water saturated nitrogen at a space velocity of 5.89 × 10$^{-4}$ ft.$^3$/sec. at 290° C yielded 9.57 g (0.085 mol) of unreacted chlorobenzene and 2.35 g (0.015 mol) of nitrochlorobenzenes. The nitrochlorobenzene consisted of 57% para and 43% ortho isomers.

EXAMPLE USING AW-500 SIEVE (PORE SIZE 5 Å)

Example H

The amounts of chlorobenzene and nitrogen dioxide as in example G at the same space velocities and water saturated nitrogen at a space velocity of 5.89 × 10$^{-4}$ ft.$^3$/sec. at 240° C yielded 8.11 g (0.072 mol) of unreacted chlorobenzene and 4.39 g (0.028 mol) of nitrochlorobenzene isomers (61% para and 39% ortho).

EXAMPLE USING AW-500 SIEVE (PORE SIZE 5 Å)

Example I

Chlorobenzene and nitrogen dioxide in the same amounts and space velocities as Example G and dry nitrogen at a space velocity of 5.89 × 10$^{-4}$ ft.$^3$/sec. at 290° C yielded 9.05 (0.08 mol) of unreacted chlorobenzene and 3.09 g (0.0196 mol) of nitrochlorobenzene isomers (58% para and 42% ortho).

EXAMPLE USING AW-500 SIEVE (PORE SIZE 5 Å)

EXAMPLE J

Chlorobenzene and nitrogen dioxide in the same amounts and space velocities as Example G and dry nitrogen at a space velocity of 7.06 × 10$^{-4}$ ft.$^3$/sec. at 290° C yielded 9.86 g (0.0876 mol) of unreacted chlorobenzene and 1.95 g (0.0124 mol) of nitrochlorobenzene isomers (56% para and 44% ortho).

EXAMPLE USING AW-500 SIEVE (PORE SIZE 5 Å)

Example K chlorobenzene, nitrogen dioxide and dry nitrogen at the same amounts and space velocities as in Example I at 240° C yielded 9.53 g (0.0847 mol) of unreacted chlorobenzene and 2.41 g (0.0153 mol) of nitrochlorobenzene isomers (60% para and 40% ortho).

EXAMPLE USING ZEOLON 300 (PORE SIZE 4-8 Å)

Example L

Chlorobenzene and nitrogen dioxide in the same amounts and at the same space velocities as in Example G and dry nitrogen at a space velocity of 2.35 × 10$^{-4}$ ft.$^3$/sec. at 235° C yielded 9.11 g (0.081 mol) of unreacted chlorobenzene, 1.42 g (0.0126 mol) of nitrochlorobenzenes (62% para, 29% ortho and 9% meta) and 0.09 g (0.006 mol) of dichlorobenzenes.

EXAMPLE USING ZEOLON 300 (PORE SIZE 4-8 Å)

Example M

Chlorobenzene and nitrogen dioxide in the same amounts and space velocities as in Example G and dry nitrogen at a space velocity of 3.53 × 10$^{-4}$ ft.$^3$/sec. at 235° C yielded 7.65 g (0.068 mol) of unreacted chlorobenzene, 0.28 g (0.0019 mol) of dichlorobenzenes and 4.88 g (0.031 mol) of nitrochlorobenzenes (77% para and 23% ortho).

EXAMPLE USING ZEOLON 300 (PORE SIZE 4-8 Å)

Example N

Chlorobenzene, nitrogen dioxide and dry nitrogen in the same amounts and space velocities as in Example L at 280° C yielded 8.81 (0.078 mol) of unreacted chlorobenzene and 3.42 g (0.022 mol) of nitrochlorobenzene isomers (79% para and 21% ortho).

EXAMPLE USING ZEOLON 300 (PORE SIZE 4-8 Å)

EXAMPLE O

Chlorobenzene, nitrogen dioxide and dry nitrogen at the same amounts and space velocities as Example M at 280° C yielded 8.63 g (0.0767 mol) of unreacted chlorobenzene, 0.28 g (0.0019 mol) of dichlorobenzenes and 3.37 g (0.0213 mol) of nitrochlorobenzenes (58% para, 25% ortho and 17% meta).

EXAMPLE USING ZEOLON 300 (PORE SIZE 4-8 Å)

Example P

Chlorobenzene and nitrogen dioxide at the same amounts and space velocities as Example M and dry nitrogen at a space velocity of 4.71 × 10$^{-4}$ ft. /sec. at 280° C yielded 7.98 g (0.0709 mol) of unreacted chlorobenzene, 0.22 g (0.0015 mol) of dichlorobenzenes and 4.36 g (0.0277 mol) of nitrochlorobenzene isomers (56% para, 29% ortho and 15% meta).

EXAMPLE USING 13X MOLECULAR SIEVE (10 Å PORE SIZE)

Example Q

Chlorobenzene and nitrogen dioxide at the same amounts and space velocities as Example G and water saturated nitrogen at a space velocity of 1.18 × 10$^{-4}$ ft.$^3$/sec. at 192° C yielded 7.45 g (0.0662 mol) of unreacted chlorobenzene, 0.31 g (0.0021 mol) of dichlorobenzenes and 4.99 g. (0.0317 mol) of nitrochlorobenzene isomers (47% para, 16% ortho and 37% meta).

EXAMPLE USING 13X MOLECULAR SIEVE (10 Å PORE SIZE)

Example R

Chlorobenzene and nitrogen dioxide at the same amounts and space velocities as Example G and water saturated nitrogen at a space velocity of 2.35 × 10$^{-4}$ ft.$^3$/sec. at 192° C yielded 8.15 g (0.0724 mol) of unreacted chlorobenzene, 0.15 g (0.001 mol) of dichlorobenzenes and 4.19 g (0.0266 mol) of nitrochlorobenzene isomers (54% para, 19% ortho and 27% meta).

EXAMPLE USING 13X MOLECULAR SIEVE (10 Å PORE SIZE)

Example S

Chlorobenzene and nitrogen dioxide at the same amounts and space velocities as Example G and water saturated nitrogen at a space velocity of 2.65 × 10$^{-4}$ ft.$^3$/sec. at 240° C yielded 10.27 g (0.0913 mol) of unreacted chlorobenzene, 0.38 g (0.0026 mol) of dichlorobenzenes, and 0.96 g (0.0061 mol) of nitrochlorobenzene isomers (62% para and 38% ortho).

EXAMPLE USING 13X MOLECULAR SIEVE (10 Å PORE SIZE)

Example T

Chlorobenzene and nitrogen dioxide at the same amounts and space velocities as Example G and water saturated nitrogen at a space velocity of $3.24 \times 10^{-4}$ ft.$^3$/sec. at 240° C yielded 10.32 g (0.0917 mol) of unreacted chlorobenzene, 0.37 g (0.0025 mol) of dichlorobenzenes and 0.90 g (0.0057 mol) of nitrochlorobenzene isomers (70% para and 30% ortho).

EXAMPLE USING 13X MOLECULAR SIEVE (10 Å PORE SIZE)

Example U

Chlorobenzene, nitrogen dioxide and dry nitrogen at the same space velocities as Example S at 240° yielded 10.32 g (0.0917 mol) of unreacted chlorobenzene, 0.02 g (0.0001 mol) of dichlorobenzenes and 1.28 g (0.0081 mol) of nitrochlorobenzene isomers (60% para and 40% ortho).

EXAMPLE USING 13X MOLECULAR SIEVE (10 Å PORE SIZE)

Example V

Chlorobenzene nitrogen dioxide and dry nitrogen in the same amounts and at the same space velocities as Example T at 240° yielded 10.09 g (0.0897 mol) of unreacted chlorobenzene and 1.62 g (0.0103 mol) of nitrochlorobenzene isomers (62% para and 38% ortho).

Example W

By way of comparison with the molecular sieves used in the above examples, various other molecular sieves having pore sizes of about 5 Å or smaller (Linde 3A, Linde 5A and Zeolon 900 sodium form) or larger than about 10 Å (macroporous silica and aluminas) yielded no nitrochlorobenzene isomers at temperatures of 190°, 240°, and 290° C and space velocities of $1.45 \times 10^{-5}$ ft.$^3$/sec. for chlorobenzene, $3.53 \times 10^{-5}$ ft.$^3$/sec. for nitrogen dioxide and $1.18 \times 10^{-4}$ to $7.06 \times 10^{-4}$ ft.$^3$/sec. for nitrogen.

Various other examples will be apparent to the person skilled in the art after reading the present disclosure without departing from the spirit and scope of the invention. All such further examples are included within the scope of the appended claims.

What is claimed is:

1. A method for the production of a nitrochlorobenzene mixture in which the para:ortho isomer distribution can be readily controlled to predetermined relative proportions within a broad range comprising the vapor phase nitration of chlorobenzene with a nitrating agent in the presence of a molecular sieve catalyst having a relatively small pore size ranging from about 5 Å to about 10 Å.

2. The method of claim 1 in which the nitrating agent is $NO_2$.

3. The method of claim 1 in which the vapor phase reaction is carried out at a temperature ranging from about 190° to about 290° C.

4. The method of claim 1 in which from about one to about three moles of nitrating agent are used per mole of chlorobenzene.

5. The method of claim 1 in which the chlorobenzene is admixed with nitrogen carrier gas prior to reaction with the nitrating agent.

6. The method of claim 5 in which the nitrogen is saturated with water vapor.

7. The method of claim 1 in which the nitrating agent is $NO_2$, the temperature ranges from about 190° to about 290° C and from about one to about three moles of $NO_2$ are used per mole of chlorobenzene.

* * * * *